United States Patent
Lin et al.

(10) Patent No.: US 12,329,493 B2
(45) Date of Patent: Jun. 17, 2025

(54) WOUND ANALYZING SYSTEM AND METHOD

(71) Applicant: NATIONAL CHENG KUNG UNIVERSITY, Tainan (TW)

(72) Inventors: Chih-Lung Lin, Tainan (TW); Meng-Hsuan Wu, Tainan (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 540 days.

(21) Appl. No.: 17/823,519

(22) Filed: Aug. 31, 2022

(65) Prior Publication Data
US 2023/0255492 A1    Aug. 17, 2023

Related U.S. Application Data

(60) Provisional application No. 63/267,939, filed on Feb. 13, 2022.

(51) Int. Cl.
*A61B 5/00* (2006.01)
*A61B 5/1455* (2006.01)

(52) U.S. Cl.
CPC ........ *A61B 5/0059* (2013.01); *A61B 5/14551* (2013.01); *A61B 5/445* (2013.01)

(58) Field of Classification Search
CPC ... A61B 5/0059; A61B 5/0075; A61B 5/1455; A61B 5/14551; A61B 5/441; A61B 5/445
See application file for complete search history.

(56) References Cited

U.S. PATENT DOCUMENTS

| | | | |
|---|---|---|---|
| 10,258,252 B1 | 4/2019 | Cudney | |
| 11,185,280 B2 * | 11/2021 | Nejati | A61B 5/445 |
| 2015/0150457 A1 * | 6/2015 | Wu | A61B 5/445 |
| | | | 600/425 |

(Continued)

FOREIGN PATENT DOCUMENTS

| | | |
|---|---|---|
| CN | 106164929 A | 11/2016 |
| CN | 112716452 A | 4/2021 |
| TW | M620589 U | 12/2021 |

OTHER PUBLICATIONS

Hsin-Yi Tsai et al., "A Noncontact Skin Oxygen-Saturation Imaging System for Measuring Human Tissue Oxygen Saturation", IEEE Transactions On Instrumentation and Measurement, vol. 63, No. 11, Nov. 2014, pp. 2620-2631.

(Continued)

*Primary Examiner* — Eric F Winakur
(74) *Attorney, Agent, or Firm* — CKC & Partners Co., LLC (57) ABSTRACT

A wound analyzing system is provided. An illumination device provides visible light and infrared light. An image sensor captures an infrared-light image, a red-light image and a visible-light image about a wound. A processor performs an image segmentation algorithm on the visible-light image to obtain a wound part and a background part, and classifies the wound part into one of multiple types. The processor calculates a blood-oxygen-concentration image according to the red-light image and the infrared-light image, aligns the visible-light image and the blood-oxygen-concentration image, and calculates a wound index and a wound healing stage according to the blood oxygen concentration values and the type corresponding to the wound part.

15 Claims, 6 Drawing Sheets

(56) References Cited

U.S. PATENT DOCUMENTS

| | | | |
|---|---|---|---|
| 2016/0069743 A1* | 3/2016 | McQuilkin | A61B 5/0075 |
| | | | 356/416 |
| 2019/0008387 A1* | 1/2019 | Godavarty | A61B 5/445 |
| 2020/0330028 A1 | 10/2020 | Nejati | |
| 2023/0181042 A1* | 6/2023 | Fan | A61B 5/445 |
| | | | 424/78.06 |

OTHER PUBLICATIONS

Rashmi Mukherjee et al., "Automated Tissue Classification Framework for Reproducible Chronic Wound Assessment", Jul. 8, 2014., pp. 1-9, vol. 2014, Biomed Research International.

Chinmay Chakraborty, "Computational approach for chronic wound tissue characterization", Feb. 22, 2019, pp.1-10, Informatics in Medicine Unlocked.

Ming-Ching Chang et al., "Multimodal Sensor system for Pressure Ulcer Wound Assessment and Care" Mar. 2018, pp. 1186-1196, vol. 14, No. 3, IEEE Transactions on Industrial Informatics.

E.A. Robledo et al., "Physiological wound assessment from coregistered and segmented tissue hemoglobin maps" Aug. 2020, pp. 1249-1256, vol. 37, No. 8, Journal of the Optical Society of America A.

Rebecca Kwasinski et al., "Tissue Oxygenation Changes to Assess Healing in Venous Leg Ulcers Using Near-Infrared Optical Imaging" 2019, pp. 565-579, vol. 8, No. 11, Advances in Wound Care.

\* cited by examiner

WOUND ANALYZING SYSTEM AND METHOD

RELATED APPLICATIONS

This application claims priority to U.S. Provisional Application Ser. No. 63/267,939 filed Feb. 13, 2022, which is herein incorporated by reference.

BACKGROUND

Field of Invention

The present invention relates to a wound analyzing system and a wound analyzing method by combining blood oxygen concentration and a visible-light image.

Description of Related Art

Chronic wound care for the elderly or diabetics is an important medical issue. These chronic wounds can affect the life quality of patients, or cause long-term bed rest and limb amputation. For these patients with chronic wounds, long-term wound monitoring and appropriate treatments are necessary. However, inspection by medical personnel requires plenty of time and increases the workload. Besides, divergent wound diagnosis made by different medical personnel could cause prolonged wound recovery time. An auxiliary wound analyzing system and method is a topic of concern to those skilled in the field.

SUMMARY

Embodiments of the present disclosure provide a wound analyzing system including an illumination device, an image sensor, and a processor. The illumination device provides visible light and infrared light. The image sensor captures an infrared-light image, a red-light image and a visible-light image with respect to a wound. The processor performs an image segmentation algorithm to the visible-light image to obtain a wound part and a background part of the visible-light image, and classifies the wound part into one of multiple types. The processor calculates a blood-oxygen-concentration image according to the red-light image and the infrared-light image. The blood-oxygen-concentration image includes multiple blood oxygen concentration values. The processor aligns the visible-light image and the blood-oxygen-concentration image, and calculates a wound index and a wound healing stage according to the blood oxygen concentration values and the type corresponding to the wound part.

In some embodiments, the wound analyzing system further includes a communication circuit electrically connected to the processor and a server communicatively connected to the communication circuit. The processor transmits the wound index and the wound healing stage to the server through the communication circuit.

In some embodiments, the types includes granulation tissue, slough tissue, necrotic tissue, and epithelial.

In some embodiments, the processor compares a first mean of the blood oxygen concentration values corresponding to the wound part with a second mean of the blood oxygen concentration values corresponding to the background part. If a difference between the first mean and the second mean is within a first predetermined range, the processor is configured to set a score to be a first value. If the first mean is greater than the second mean and the difference is out of the first predetermined range, the processor is configured to set the score to be a second value. If the first mean is less than the second mean and the difference is out of the first predetermined range, the processor is configured to determine if the first mean is less than the second mean by a predetermined value, and then generate a warning message if affirmative, otherwise set the score to be a third value.

In some embodiments, the processor is configured to calculate the wound index according to the following equation where Index is the wound index, $C_0$ is a constant, $P_i$ is a confidence value of $i^{th}$ type of the wound part, $W_i$ is a weight of the $i^{th}$ type, and Score is the score.

$$Index = \Sigma_i C_0 \times P_i \times W_i \times Score$$

In some embodiments, if the confidence value of the type of epithelial is greater than a threshold, the processor is configured to set the wound healing stage to be remodeling. If the confidence value of the type of granulation tissue is greater than the confidence value of the type of slough tissue and the confidence value of the type of necrotic tissue, the processor is configured to set the wound healing stage to be proliferative, otherwise set the wound healing stage to be inflammatory.

In some embodiments, the processor is configured to compare a first area of the wound part with a second area of a previous wound part. If a difference between the first area and the second area is within a second predetermined range, the processor is configured to set an area score to be a fourth value. If the first area is greater than the second area and the difference is out of the second predetermined range, the processor is configured to set the area score to be a fifth value. If the first area is less than the second area and the difference if out of the second predetermined range, the processor is configured to set the area score to be a sixth value.

In some embodiments, the processor is configured to determine if the confidence values of each of the types of the wound part increases compared to confidence values of types of the previous wound part. If the confidence values of the types of granulation tissue and epithelial increase, the processor is configured to set a healing score according to an increasing amount thereof. If the confidence values of the types of necrotic tissue and slough tissue increase, the processor is configured to set the healing score according to an increasing amount thereof, otherwise set the healing score to be a constant.

From another aspect, embodiments of the present disclosure provide a wound analyzing method for a processor. The wound analyzing method includes: providing, by an illumination device, visible light and infrared light; capturing, by an image sensor, an infrared-light image, a red-light image and a visible-light image with respect to a wound; performing an image segmentation algorithm to the visible-light image to obtain a wound part and a background part of the visible-light image, and classifying the wound part into one of multiple types; calculating a blood-oxygen-concentration image according to the red-light image and the infrared-light image, in which the blood-oxygen-concentration image includes multiple blood oxygen concentration values; and aligning the visible-light image and the blood-oxygen-concentration image; and calculating a wound index and a wound healing stage according to the blood oxygen concentration values and the type corresponding to the wound part.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
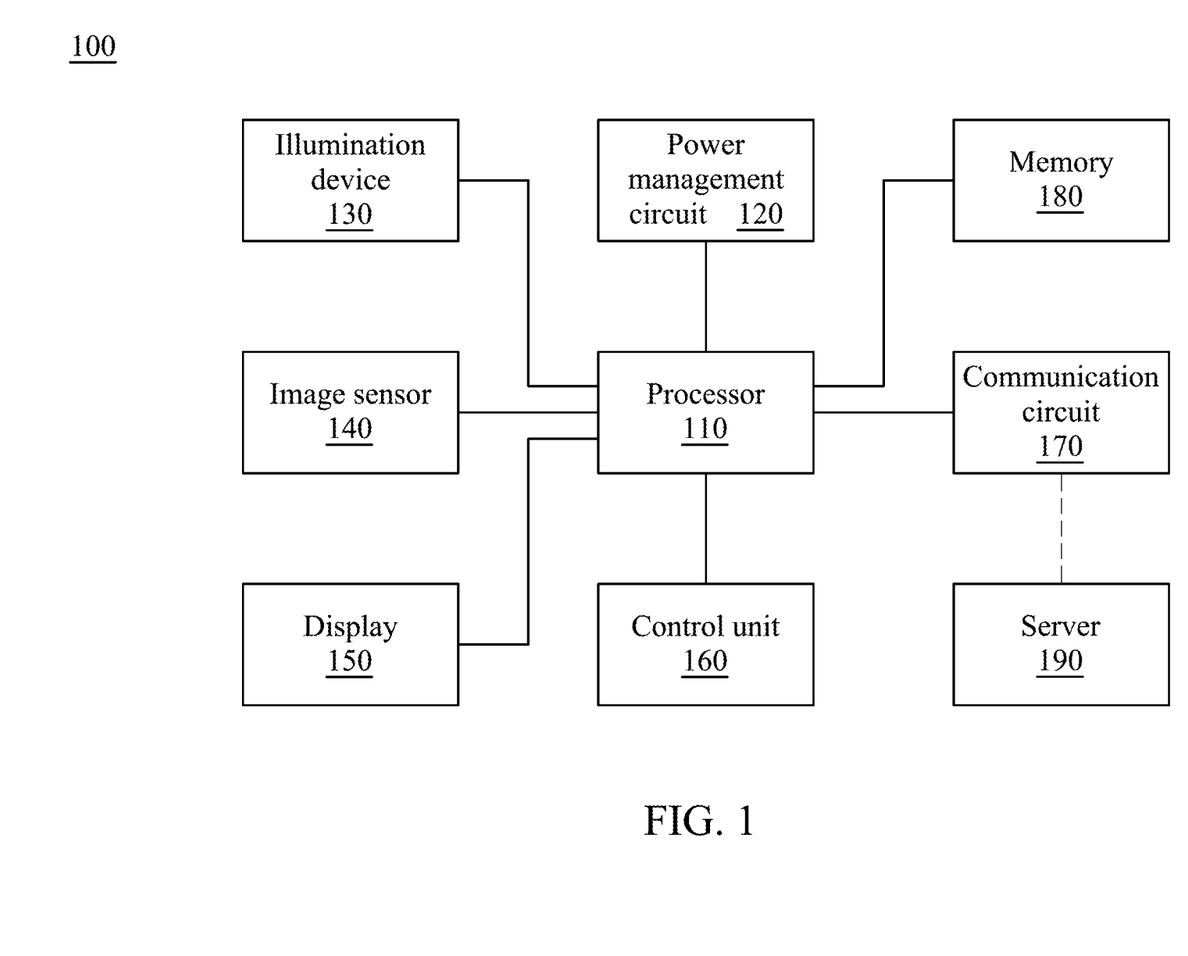
FIG. 1 is a schematic diagram of a wound analyzing system in accordance with an embodiment.

FIG. 1 is a schematic diagram of a wound analyzing system in accordance with an embodiment. Referring to FIG. 1, a wound analyzing system 100 includes a processor 110, a power management circuit 120, an illumination device 130, an image sensor 140, a display 150, a control unit 160, a communication circuit 170, a memory 180, and a server 190.

The processor 110 may be a central processing unit, a microprocessor, a microcontroller, an application specific integrated circuit, etc. The illumination device 130 may include one or more suitable lighting unit such as light emitting diode for providing visible light and infrared light. In some embodiments, the visible light includes red light and white light. The wavelength of the red light is, for example, 660 nm. The wavelength of the infrared light is, for example, 880 nm. However, the wavelengths of the visible light and the infrared light are not limited in the disclosure.

The image sensor 140 may include a charge-coupled device (CCD) sensor, a complementary metal-oxide semiconductor (CMOS) sensor, or any other suitable sensors. In some embodiments, the image sensor 140 may include duo-cameras or any device capable of sensing depths of the field. In some embodiments, the image sensor 140 may include a thermal image sensor. The image sensor 140 may include different sensors for the spectrum of the red light, the visible light and the infrared light so as to generate a red-light image, a visible-light image, and an infrared-light image. For example, the red-light image is captured when the red light is provided, the visible-light image (also referred to as a white-light image) is captured when the white light is provided, and the infrared-light image is captured when the infrared light is provided. In some embodiments, a single broad-spectrum sensor is adopted to capture the red-light image, the visible-light image, and the infrared-light image.

The display 150 may be a liquid crystal display, an organic light emitting diode (OLED) display or any suitable display. The control unit 160 may include buttons, knobs, or any human-machine interface. The communication circuit 170 may include circuits for providing communication function of Internet, local area networks (LANs), wide area networks (WANs), cellular networks, near field communications (NFC), infrared (IR), Bluetooth, WiFi, etc. The communication circuit 170 is communicatively connected to the server 190. The memory 180 may be a volatile memory or a non-volatile memory which is not limited in the disclosure.

In some embodiments, processor 110, the power management circuit 120, the illumination device 130, the image sensor 140, the display 150, the control unit 160, the communication circuit 170, and the memory 180 are implemented in a wound analyzing device which can be carried by patients. The wound analyzing device can perform a wound analyzing method for calculating blood oxygen concentration according to the red-light image and the infrared-light image, and recognizing locations, sizes, and types of the wounds in the visible-light image. The information is combined to calculate a wound index and a wound healing stage which will be described in detail below.

Figure 2:
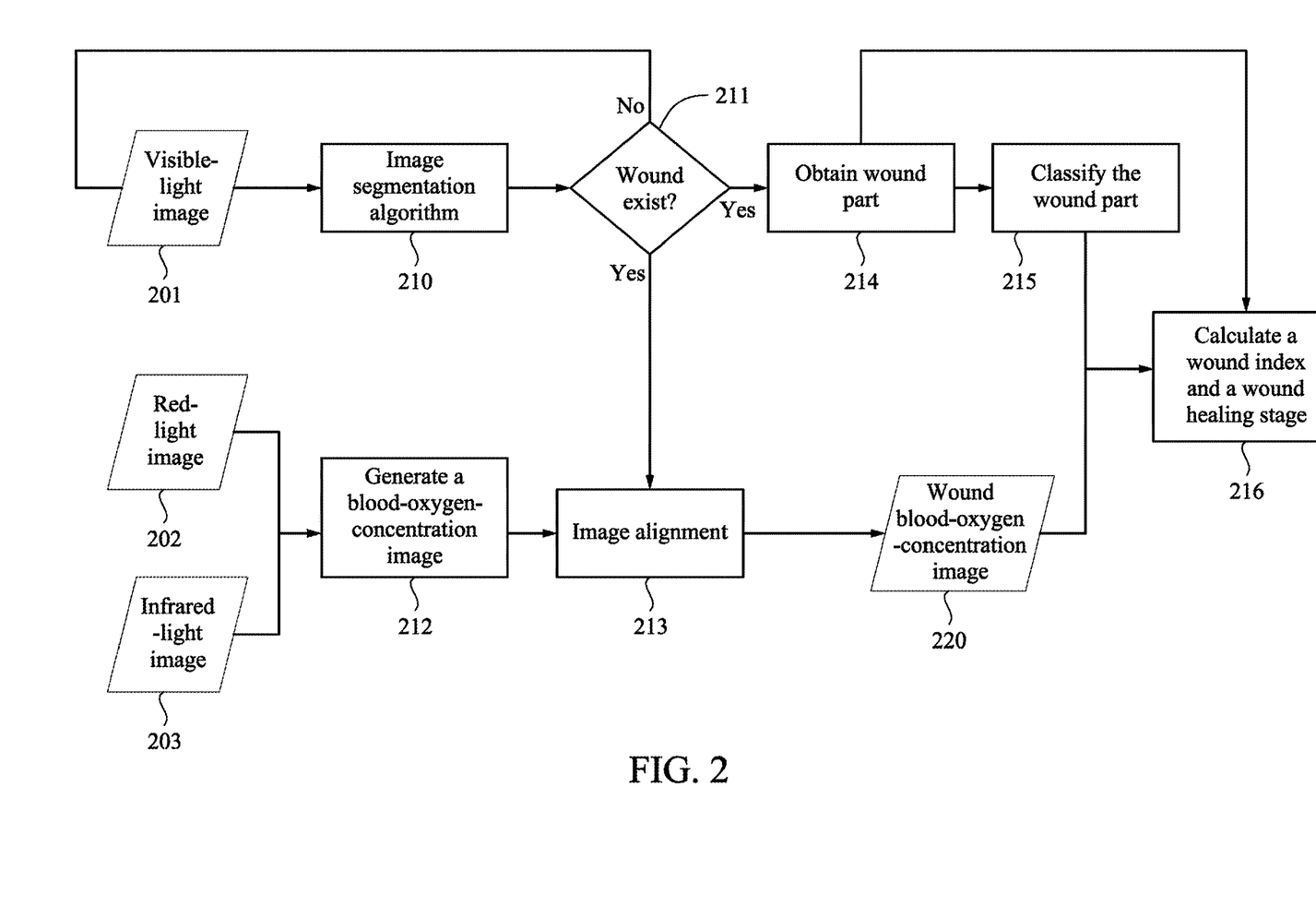
FIG. 2 is a flow chart of a wound analyzing method in accordance with an embodiment.
Figure 3:
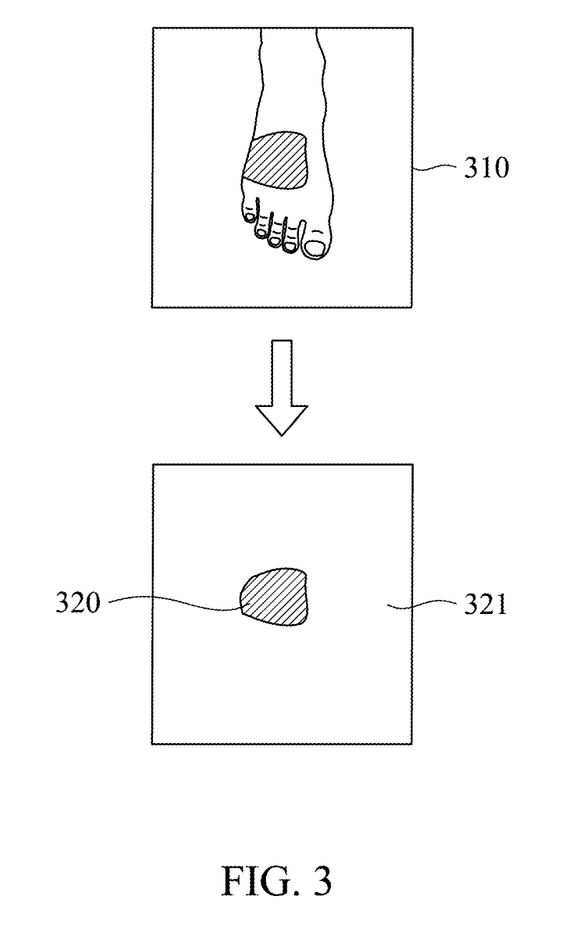
FIG. 3 is a schematic diagram of a patient's wound and an image segmentation result in accordance with an embodiment.

FIG. 2 is a flow chart of the wound analyzing method in accordance with an embodiment. Referring to FIG. 2, first, the image sensor 140 captures the visible-light image 201, the red-light image 202, and the infrared-light image 203. In step 210, an image segmentation algorithm is performed to the visible-light image 201 to obtain wound parts and background parts in the visible-light image 201. For example, referring to FIG. 3, there is a wound on a patient's foot shown in a visible-light image 310. After the image segmentation algorithm is performed, a wound part 320 and a background part 321 are obtained. In other words, the segmentation result is regarded as a mask to indicate where the wound is. In some embodiments, the background part 321 may be further classified into a skin part or other parts. The image segmentation algorithm may be any suitable machine learning model such as convolutional neural network or an image processing algorithm such as a watershed algorithm, which is not limited in the disclosure. In step 211, it is determined whether the visible-light image includes a wound, and if not, then a next visible-light image is captured.

In step 212, a blood-oxygen-concentration image is generated according to the red-light image 202 and the infrared-light image 203. The blood-oxygen-concentration image includes multiple pixels representing blood oxygen concentration values. For example, a reference of H.-Y. Tsai, K.-C. Huang, H.-C. Chang, J.-L. A. Yeh and C.-H. Chang, "A Noncontact Skin Oxygen-Saturation Imaging System for Measuring Human Tissue Oxygen Saturation," in *IEEE Transactions on Instrumentation and Measurement*, vol. 63, no. 11, pp. 2620-2631, November 2014 is herein incorporated to calculate the blood oxygen concentration values, but the disclosure is not limited thereto.

In step 213, an image alignment is performed to align the visible-light image and the blood-oxygen-concentration image. For example, features of the visible-light image and the blood-oxygen-concentration image are detected by algorithms such as scale-invariant feature transform (SIFT), edge detection, corner detection, etc. In some embodiments, one or multiple markers are disposed on the patient, and the markers are detected from the images. Next, the features or the markers are matched between the two images to calculate a homography matrix, and then a coordinate of the other image can be transformed into a coordinate of the other image based on the homography matrix. People skilled in the art should be able to perform the image alignment based on conventional algorithms of computer vision, which is not limited in the disclosure. After the step 213 is performed, a wound blood-oxygen-concentration image 220 is generated that indicates the blood oxygen concentration value of each pixel in the wound part and the background part. If a single sensor is used to capture the red-light image, the visible-light image, and the infrared-light image, then there is no displacement between the images. In this case, the visible-light image may be directly overlapped with the blood-oxygen-concentration image without calculating the homography matrix. The description of "image alignment" in the disclosure includes embodiments of calculating the homography matrix and the embodiments of overlapping the visible-light image with the blood-oxygen-concentration image.

In step 214, the wound part is obtained from the visible-light image 201 based on the image segmentation algorithm. In some embodiments, the size of the wound part is also calculated. In step 215, the wound part is classified into one of multiple types including granulation tissue, slough tissue, necrotic tissue, and epithelial. The classification may be performed based on a machine learning model such as a convolutional neural network and a support vector machine. In some embodiments, the convolutional neural network outputs four values indicating confidence values of granulation tissue, slough tissue, necrotic tissue, and epithelial respectively. The type having the greatest confidence value serves as the type of the wound part.

Figure 4:
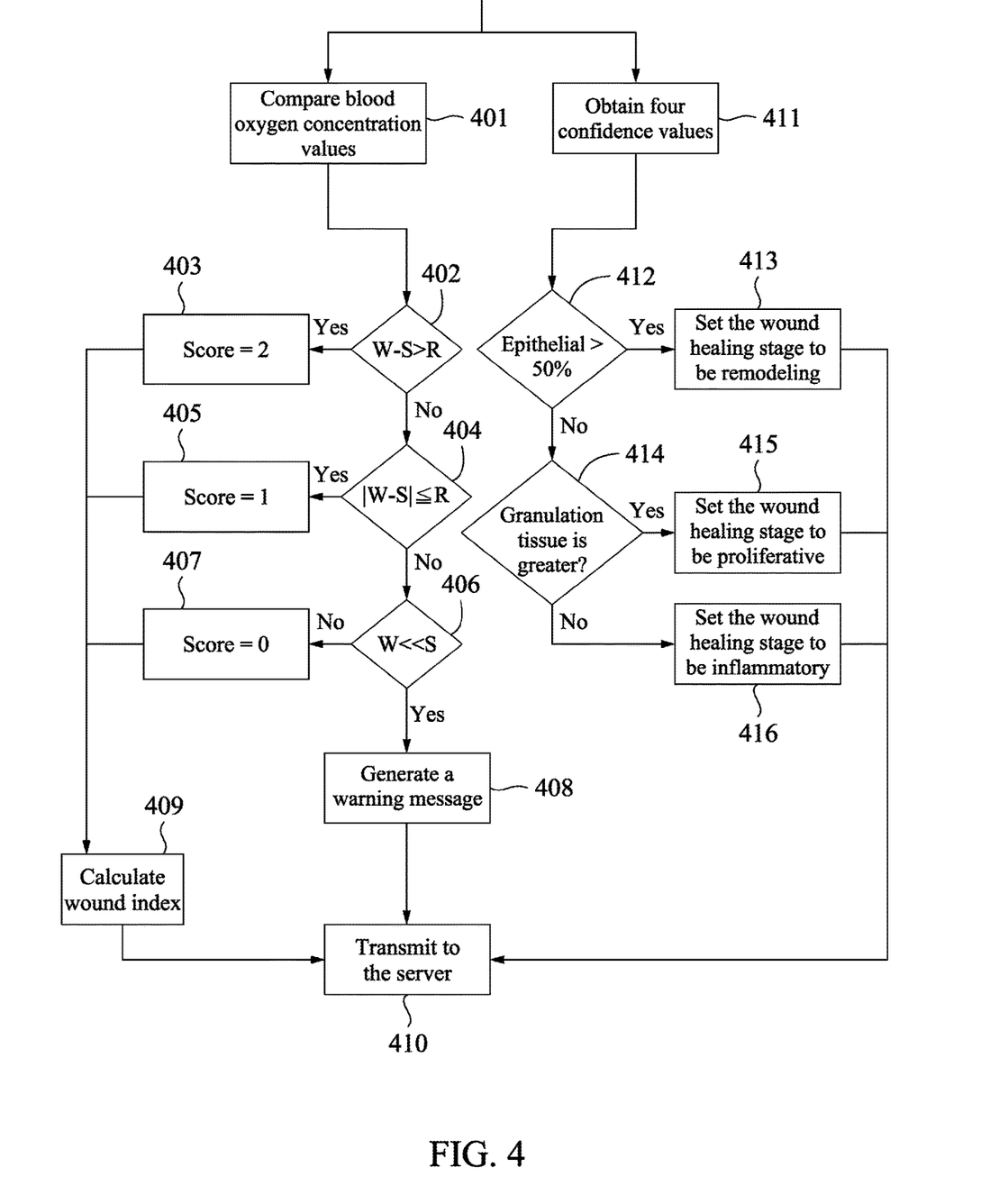
FIG. 4 is a detailed flow chart of the step 216 in accordance with an embodiment.

In step 216, the result of the step 215 is combined with the wound blood-oxygen-concentration image 220. A wound index and a wound healing stage are calculated according to the type and the blood oxygen concentration values corresponding to the wound part. FIG. 4 is a detailed flow chart of the step 216 in accordance with an embodiment. Referring to FIG. 4, in step 401, the blood oxygen concentration values of the wound part is compared with the blood oxygen concentration values of the background part. A mean (also referred to as a first mean noted as "W" hereinafter) of the blood oxygen concentration values of the wound part is calculated. A mean of the blood oxygen concentration values of the skin part is calculated, or a mean of the blood oxygen concentration values within the background part extended from the wound part by a distance is calculated. The mean of the background part is also referred to as a second mean noted as S hereinafter.

In step 402, whether the first mean W is greater than the second mean S and the difference thereof is out of a predetermined range is determined. The predetermined range is noted as ±R where R is a positive number determined by experiments. If the result of the step 402 is affirmative, then in step 403, a score is set to be a second value (e.g. 2). In step 404, whether the difference between the first mean W and the second mean S is within the predetermined range ±R is determined, and if affirmative, then the score is set to be a first value (e.g. 1) in step 405. If the result of the 404 is no, it means the first mean W is less than the second mean S and the difference thereof is out of the predetermined range, and then in step 406, whether the first mean S is way less than the second mean W is determined. To be specific, whether the first mean S is less than the second mean W by a predetermined value T is determined in which the predetermined value T is a positive number greater than R. If the result of the step 406 is no, then in step 407, the score is set to be a third value (e.g. 0); otherwise the wound may be cellulitis, and a warning message is generated in step 408.

In step 409, the wound index is calculated based on the following equation 1.

$$\text{Index} = \sum_i C_0 \times P_i \times W_i \times \text{Score} \qquad \text{[Equation 1]}$$

In the equation, Index is the wound index. Score is the said score. $C_0$ is a constant such as 10. $P_i$ is the confidence value of $i^{th}$ type of the wound part. $W_i$ is a weight of the $i^{th}$ type. In the embodiment, the weight of the type of granulation tissue is 0.5; the weight of the type of slough tissue is 0.1; the weight of the type of necrotic tissue is 0.1; and the weight of the type of epithelial is 0.5. The weights are merely examples which are not limited in the disclosure. Higher blood oxygen concentration of the wound part means the wound is recovered better. In the embodiments, greater wound index indicates better recovery situation. In the previous paragraph, the second value is 2, the first value is 1, and the third value is 0, but these values are merely examples which are not limited in the disclosure. In other embodiments, the second value, the first value, and the third value are set to be three decreasing values. In other words, the second value is greater than the first value which is greater than the third value. In step 410, the calculated wound index or the warning message is transmitted to the server 190.

In step 411, four confidence values of the types are obtained. The wound healing stage is determined according to the confidence value of each type. To be specific, in step 412, whether the confidence value of the type of epithelial is greater than a threshold (e.g. 50%) is determined. If the determination is affirmative, in step 413, the wound healing stage is set to be remodeling. If the result of the step 412 is no, in step 414, it is determined whether the confidence value of the type of granulation tissue is greater than the confidence value of the type of slough tissue and greater than the confidence value of the type of necrotic tissue. If the determination is affirmative, in step 415, the wound healing stage is set to be proliferative, otherwise the wound healing stage is set to be inflammatory in step 416. In the step 410, the wound healing stage may also be transmitted to the server 190.

Figure 5:
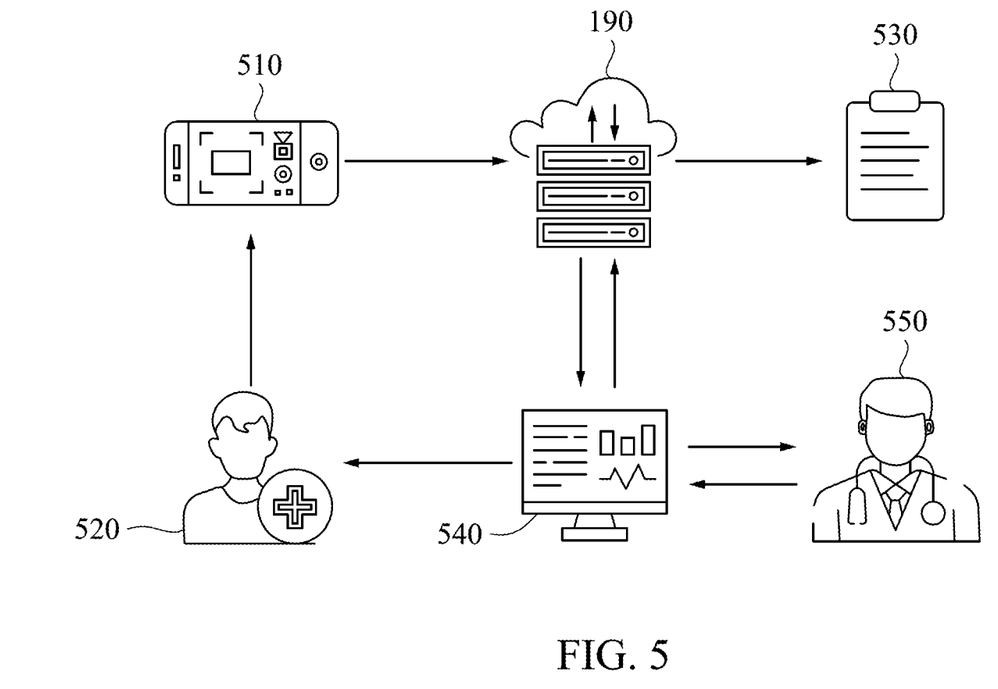
FIG. 5 is a schematic diagram of using the wound analyzing system in accordance with an embodiment.

FIG. 5 is a schematic diagram of using the wound analyzing system in accordance with an embodiment. Referring to FIG. 5, a wound analyzing device 510 captures an image of a patient 520 and performs the aforementioned method to calculate the wound index and the wound healing stage which are transmitted to the server 190 and stored in a database 530. The server 190 can provide a platform 540 through the Internet, and medical personnel 550 can read the wound index and the wound healing stage on the platform 540. The medical personnel 550 can give advice to the patient 520 through the platform 540.

Figure 6:
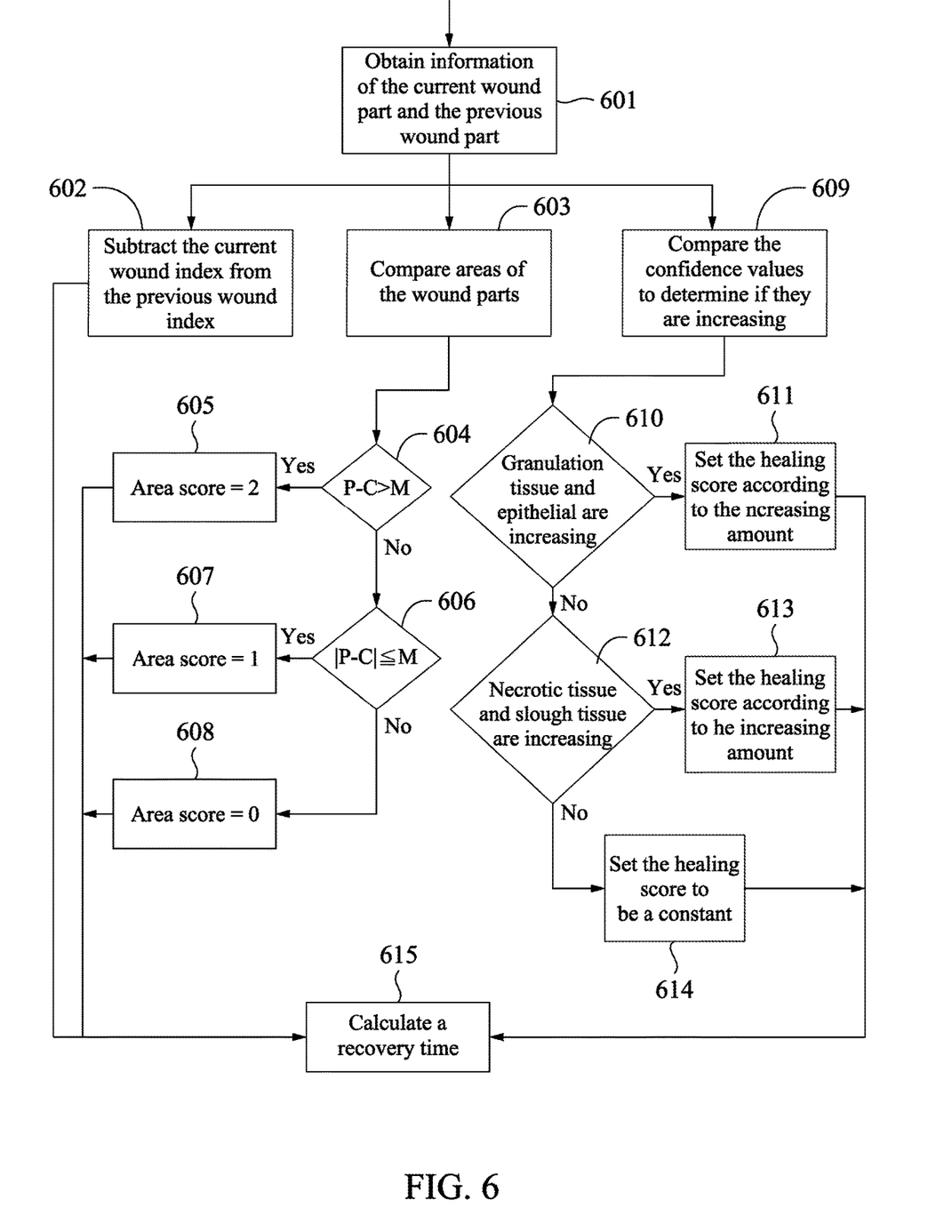
FIG. 6 is flow chart of calculating a healing score in accordance with an embodiment.

The wound index and the wound healing stage can be stored in the database 530 as history data. Every time a new wound index and a new wound healing stage are calculated, they are compared with the history data to calculate related scores. In detail, the wound part of the history data is referred to as a previous wound part. FIG. 6 is flow chart of calculating a healing score in accordance with an embodiment. Referring to FIG. 6, in step 601, information of the current wound part and the previous wound part is obtained. In step 602, the wound index of the previous wound part is subtracted from the wound index of the current wound part. In step 603, an area (also referred to a first area noted as C) of the current wound part is compared with an area (also referred to as a second area noted as P) of the previous wound part. In step 604, it is determined if the second area P is greater than the first area C and the difference is out of a predetermined range ±M where M is a positive number. If the determination is affirmative, then an area score is set to be a fifth value (e.g. 2) in step 605. If the result of the step 604 is no, then in step 606, it is determined if the difference between the first area C and the second area P is within the predetermined range ±M. If the result of the step 606 is affirmative, then in step 607, area score is set to be a fourth value (e.g. 1). If the result of the step 606 is no, it means the first area C is less than the second area P and the difference is out of the predetermined range ±M, and then in step 60, the area score is set to be a sixth value (e.g. 0). If the area of the wound part is decreasing, it represents the recovery situation is good which leads to a greater area score. In some embodiments, the fifth value, the fourth value, and the sixth value may be set as three decreasing values which are not limited in the disclosure.

In step 609, the confidence value of each type of the current wound part is compared (i.e. whether the confidence value is increasing) with the confidence value of the corresponding type of the previous wound part. In step 610, it is determined whether the confidence values of the types of granulation tissue and epithelial are both increasing. If the determination is affirmative, then in step 611, a healing score is set according to the corresponding increasing amount. In detail, the confidence values of granulation tissue and epithelial of the current wound part are added to be $Gran\_epi_{current}$. On the other hand, the confidence values of granulation tissue and epithelial of the previous wound part are added to be $Gran\_epi_{past}$. The healing score is set based on the following equation 2.

$$Score_{tissue} = C_1 \times (Gran\_epi_{current} - Gran\_epi_{past}) \quad \text{[Equation 2]}$$

In the equation 2, $C_1$ is a positive real number. If the result of the step 610 is no, then in step 612, it is determined whether the confidence values of necrotic tissue and slough tissue are both increasing. If the result of the step 612 is affirmative, healing score is set according to the increasing amount. In detail, the confidence values of necrotic tissue and slough tissue of the current wound part are added to be $Slo\_nec_{current}$. On the other hand, the confidence values of necrotic tissue and slough tissue of the previous wound part are added to be $Slo\_nec_{past}$. The healing score is set based on the following equation.

$$Score_{tissue} = C_2 \times (Slo\_nec_{current} - Slo\_nec_{past}) \quad \text{[Equation 3]}$$

In the equation 3, $C_2$ is a negative real number. In the disclosure, greater healing score indicate better recovery situation. If the result of the step 612 is no, then the healing score is set to be a constant (e.g. 0) which may be determined by experiments in step 614. In step 615, a recovery time is calculated according to the value calculated in the step 602, the area score, and the healing score. The calculation is, for example, written in the following equation 4.

$$Time = K_1 \times Index\_change + K_2 \times Score_{size} + K_3 \times Score_{tissue} \quad \text{[Equation 4]}$$

In the equation 4, Time is the recovery time. Index_change is the difference of the wound indexes calculated in the step 602. $Score_{size}$ is the area scores calculated in the steps 604-608. $K_1$, $K_2$, and $K_3$ are real numbers determined by experiments. A linear function is adopted herein to calculate the recovery time. However, in other embodiments, polynomial functions, exponential functions, or arbitrary machine learning models may be used to calculate the recovery time which is not limited in the disclosure.

In the disclosure, the mentioned machine learning model may be a decision tree, a random forest, a multilayer perception neural network, a convolutional neural network, a support vector machine, etc. The structure of the convolutional neural network may be LeNet, AlexNet, VGG, GoogLeNet, ResNet, YOLO, etc. The lost function may be mean square error (MSE), mean absolute error (MAE), cross-entropy, Huber loss function, Log-Cosh lost function, etc. The update of the parameters may be based on gradient descent, backpropagation, etc. which is not limited in the disclosure.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A wound analyzing system, comprising:
   an illumination device configured to provide visible light and infrared light;
   an image sensor configured to capture an infrared-light image, a red-light image and a visible-light image with respect to a wound; and
   a processor configured to perform an image segmentation algorithm to the visible-light image to obtain a wound part and a background part of the visible-light image, and classify the wound part into one of a plurality of types,
   wherein the processor is configured to calculate a blood-oxygen-concentration image according to the red-light image and the infrared-light image, wherein the blood-oxygen-concentration image comprises a plurality of blood oxygen concentration values,
   wherein the processor is configured to align the visible-light image and the blood-oxygen-concentration image, and calculate a wound index and a wound healing stage according to the blood oxygen concentration values and the type corresponding to the wound part.

2. The wound analyzing system of claim 1, further comprising:
   a communication circuit electrically connected to the processor; and
   a server communicatively connected to the communication circuit,
   wherein the processor is configured to transmit the wound index and the wound healing stage to the server through the communication circuit.

3. The wound analyzing system of claim 1, wherein the types comprises granulation tissue, slough tissue, necrotic tissue, and epithelial.

4. The wound analyzing system of claim 3, wherein the processor is configured to compare a first mean of the blood oxygen concentration values corresponding to the wound part with a second mean of the blood oxygen concentration values corresponding to the background part, if a first difference between the first mean and the second mean is within a first predetermined range, the processor is configured to set a score to be a first value;

if the first mean is greater than the second mean and the first difference is out of the first predetermined range, the processor is configured to set the score to be a second value; and if the first mean is less than the second mean and the first difference is out of the first predetermined range, the processor is configured to determine if the first mean is less than the second mean by a predetermined value, and then generate a warning message if affirmative, otherwise set the score to be a third value.

5. The wound analyzing system of claim 4, wherein the processor is configured to calculate the wound index according to a following equation:

$$\text{Index}=\Sigma_i C_0 \times P_i \times W_i \times \text{Score}$$

wherein Index is the wound index, $C_0$ is a constant, $P_i$ is a confidence value of $i^{th}$ type of the wound part, $W_i$ is a weight of the $i^{th}$ type, and Score is the score.

6. The wound analyzing system of claim 5, wherein if the confidence value of the type of epithelial is greater than a threshold, the processor is configured to set the wound healing stage to be remodeling, If the confidence value of the type of granulation tissue is greater than the confidence value of the type of slough tissue and the confidence value of the type of necrotic tissue, the processor is configured to set the wound healing stage to be proliferative, otherwise set the wound healing stage to be inflammatory.

7. The wound analyzing system of claim 6, wherein the processor is configured to compare a first area of the wound part with a second area of a previous wound part, if a second difference between the first area and the second area is within a second predetermined range, the processor is configured to set an area score to be a fourth value;

if the first area is greater than the second area and the second difference is out of the second predetermined range, the processor is configured to set the area score to be a fifth value; and if the first area is less than the second area and the second difference if out of the second predetermined range, the processor is configured to set the area score to be a sixth value.

8. The wound analyzing system of claim 7, wherein the processor is configured to determine if the confidence value of each of the types of the wound part increases compared to a confidence value of a type of the previous wound part, if the confidence values of the types of granulation tissue and epithelial increase, the processor is configured to set a healing score according to an increasing amount thereof; and if the confidence values of the types of necrotic tissue and slough tissue increase, the processor is configured to set the healing score according to an increasing amount thereof, otherwise set the healing score to be a first constant.

9. A wound analyzing method for a processor, the wound analyzing method comprising:

providing, by an illumination device, visible light and infrared light;

capturing, by an image sensor, an infrared-light image, a red-light image and a visible-light image with respect to a wound;

performing an image segmentation algorithm to the visible-light image to obtain a wound part and a background part of the visible-light image, and classifying the wound part into one of a plurality of types;

calculating a blood-oxygen-concentration image according to the red-light image and the infrared-light image, wherein the blood-oxygen-concentration image comprises a plurality of blood oxygen concentration values;

aligning the visible-light image and the blood-oxygen-concentration image; and calculating a wound index and a wound healing stage according to the blood oxygen concentration values and the type corresponding to the wound part.

10. The wound analyzing method of claim 9, wherein the types comprises granulation tissue, slough tissue, necrotic tissue, and epithelial.

11. The wound analyzing method of claim 10, further comprising:

comparing a first mean of the blood oxygen concentration values corresponding to the wound part with a second mean of the blood oxygen concentration values corresponding to the background part;

if a first difference between the first mean and the second mean is within a first predetermined range, setting a score to be a first value;

if the first mean is greater than the second mean and the first difference is out of the first predetermined range, setting the score to be a second value; and if the first mean is less than the second mean and the first difference is out of the first predetermined range, determining if the first mean is less than the second mean by a predetermined value, and then generating a warning message if affirmative, otherwise setting the score to be a third value.

12. The wound analyzing method of claim 11, further comprising:

calculating the wound index according to a following equation:

$$\text{Index}=\Sigma_i C_0 \times P_i \times W_i \times \text{Score}$$

wherein Index is the wound index, $C_0$ is a constant, $P_i$ is a confidence value of $i^{th}$ type of the wound part, $W_i$ is a weight of the $i^{th}$ type, and Score is the score.

13. The wound analyzing method of claim 12, further comprising:

if the confidence value of the type of epithelial is greater than a threshold, setting the wound healing stage to be remodeling; and If the confidence value of the type of granulation tissue is greater than the confidence value of the type of slough tissue and the confidence value of the type of necrotic tissue, to setting the wound healing stage to be proliferative, otherwise setting the wound healing stage to be inflammatory.

14. The wound analyzing method of claim 13, further comprising:

comparing a first area of the wound part with a second area of a previous wound part;

if a second difference between the first area and the second area is within a second predetermined range, setting an area score to be a fourth value;

if the first area is greater than the second area and the second difference is out of the second predetermined range, setting the area score to be a fifth value; and if the first area is less than the second area and the second difference if out of the second predetermined range, setting the area score to be a sixth value.

15. The wound analyzing method of claim 14, further comprising:
- determining if the confidence value of each of the types of the wound part increases compared to a confidence value of a type of the previous wound part;
- if the confidence values of the types of granulation tissue and epithelial increase, setting a healing score according to an increasing amount thereof; and
- if the confidence values of the types of necrotic tissue and slough tissue increase, setting the healing score according to an increasing amount thereof, otherwise setting the healing score to be a first constant.

* * * * *